US011185358B2

(12) United States Patent
Notrica

(10) Patent No.: US 11,185,358 B2
(45) Date of Patent: Nov. 30, 2021

(54) APPARATUS AND METHODS FOR TREATING PECTUS EXCAVATUM

(71) Applicant: David M. Notrica, Phoenix, AZ (US)

(72) Inventor: David M. Notrica, Phoenix, AZ (US)

(73) Assignee: MEDICAL DESIGN INNOVATION, LLC, Phoenix, AZ (US)

( * ) Notice: Subject to any disclaimer, the term of this patent is extended or adjusted under 35 U.S.C. 154(b) by 613 days.

(21) Appl. No.: 16/118,176

(22) Filed: Aug. 30, 2018

(65) Prior Publication Data

US 2019/0059964 A1 Feb. 28, 2019

Related U.S. Application Data

(60) Provisional application No. 62/552,699, filed on Aug. 31, 2017.

(51) Int. Cl.
*A61B 17/80* (2006.01)
*A61B 17/84* (2006.01)
*A61B 17/88* (2006.01)
*A61B 17/68* (2006.01)

(52) U.S. Cl.
CPC ......... *A61B 17/8076* (2013.01); *A61B 17/84* (2013.01); *A61B 17/8863* (2013.01); *A61B 2017/681* (2013.01)

(58) Field of Classification Search
CPC ................. A61B 17/8076; A61B 17/8863
See application file for complete search history.

(56) References Cited

U.S. PATENT DOCUMENTS

| 5,092,893 | A | * | 3/1992 | Smith | A61F 2/4455 606/290 |
| 6,024,759 | A | | 2/2000 | Nuss et al. | |
| 2004/0117016 | A1 | * | 6/2004 | Abramson | A61B 17/8076 623/16.11 |
| 2006/0058786 | A1 | | 3/2006 | Kim et al. | |
| 2011/0251540 | A1 | | 10/2011 | Notrica | |
| 2017/0156759 | A1 | | 6/2017 | Park | |
| 2018/0310973 | A1 | * | 11/2018 | Son | A61B 17/8076 |
| 2021/0022782 | A1 | * | 1/2021 | Martinez Ferro | A61B 17/808 |

FOREIGN PATENT DOCUMENTS

| FR | 2353274 A1 * | 12/1977 | ......... A61B 17/8085 |
| RU | 2496438 C2 | 10/2013 | |
| WO | WO-2005055844 A1 * | 6/2005 | ......... A61B 17/8076 |

OTHER PUBLICATIONS

International Preliminary Report on Patentability, PCT/US18/48928 dated Mar. 3, 2020; 7 pgs.
International Search Report, PCT/US18/48928; dated Nov. 9, 2018; 3 pgs.
Written Opinion, PCT/US18/48928; dated Nov. 9, 2018; 6 pgs.

* cited by examiner

*Primary Examiner* — Matthew J Lawson
(74) *Attorney, Agent, or Firm* — Daniel R. Pote

(57) ABSTRACT

Various embodiments provide an apparatus for treating pectus excavatum. A pectus bar apparatus includes at least one elongated bar having an offset bend between a first end and a second end, at least one aperture near the first end and at least one aperture near the second end, a planar stabilizer extending orthogonally from the elongated bar, and a pair of opposing rib reveals located between the first end and the planar stabilizer. A pectus excavatum treatment kit and a method for utilizing that kit are also provided.

12 Claims, 17 Drawing Sheets

APPARATUS AND METHODS FOR TREATING PECTUS EXCAVATUM

RELATED APPLICATIONS

This application claims the benefit of and priority to U.S. Provisional Patent Application Ser. No. 62/552,699, filed Aug. 31, 2017, and entitled "Apparatus and Methods for Treating Pectus Excavatum," the contents of which are incorporated herein by reference.

TECHNICAL FIELD

The present invention relates, generally, to medical devices and, more particularly, to apparatus and methods for treating pectus excavatum.

BACKGROUND

Pectus excavatum is a malformation of the chest wall that causes a depression in the chest. The depressed chest walls can compress the heart or lungs, which limits physical activity and can ultimately cause malfunction of the respiratory organs. In case of children, the compressed respiratory organs can limit or delay the growth of a child and can increase the risk of pneumonia and other respiratory ailments.

Treatment techniques for pectus excavatum were developed by a team of doctors working with Dr. Donald Nuss (see, for example, U.S. Pat. No. 6,024,759). Using the Nuss Procedure, a surgeon positions one or more concave steel bars, known to the medical community as "pectus bars," inside the chest and underneath the sternum. The concave pectus bar or bars are then flipped to a convex position to force the deformed sternum outward, which preferably corrects the depression in the chest wall. The ends of the pectus bar are attached to the nearest rib using sutures or metal wire. The pectus bar typically stays in the body for approximately two years. In children, however, a pectus bar may remain in the body for up to five years. After the rib cage has been stabilized and the bones have solidified into place, the pectus bar is removed.

One of the shortcomings of the Nuss Procedure is that the pectus bar or bars have a tendency to flip out of position, which is very painful for the patient. Even though each of the ends of the pectus bar is attached to a rib, the flip rate of pectus bars has been reported to be as high as 15%.

Recent improvements to the Nuss Procedure have included stabilizers, which can be attached to the pectus bar. The stabilizers include a channel, which is sized to slide onto the pectus bar. In practice, a pair of stabilizers are placed onto either end of the implanted pectus bar. In some procedures, each stabilizer is secured with sutures to the supporting structure, which is typically cartilage. In a more cumbersome procedure, each stabilizer is attached with wire to one or more of the ribs.

Over time, the repetitive stress from movement of pectus bars can cause the wire to stimulate inflammation in surrounding tissue or to fracture and erode through the skin.

If two pectus bars are used in a procedure, the stabilizer has two channels, which are sized to receive the ends of the two bars. During the procedure, a pair of the stabilizers with two channels are connected onto either end of the pair of pectus bars to form a rectangular cage. This procedure requires large incisions on either side of the thorax to allow insertion of the stabilizer through the skin and then lining up and attaching the stabilizer.

One drawback of current stabilizers is the rubbing together of the pectus bars when a patient breathes, which can be accompanied by an audible clicking noise. Current pectus bars can also cause pain along the ribs from the pinching of the intercostal nerve at the contact point of the pectus bar in contact with the rib. Pain during breathing can be caused by the intercostal nerve of a rib moving across the pectus bar.

Systems and methods are thus needed which overcome these and other limitations of the prior art. Various desirable features and characteristics will also become apparent from the subsequent detailed description and the appended claims, taken in conjunction with the accompanying drawings and this background section.

BRIEF SUMMARY

Various embodiments of the present invention relate to i) an improved pectus bar assembly having at least one elongated bar having an offset bend between a first end and a second end, at least one aperture near the first end and at least one aperture near the second end, a planar stabilizer extending orthogonally from the elongated bar, and a pair of opposing rib reveals located between the first end and the planar stabilizer; ii) a minimally invasive method of deploying a pectus bar assembly as described herein; iii) a pectus bar kit including all the materials and tools necessary to deploy the pectus bar assembly as described herein.

Other embodiments, aspects, and features are described in greater detail below.

BRIEF DESCRIPTION OF THE DRAWING FIGURES

Exemplary embodiments will hereinafter be described in conjunction with the following drawing figures.

Figure 1:
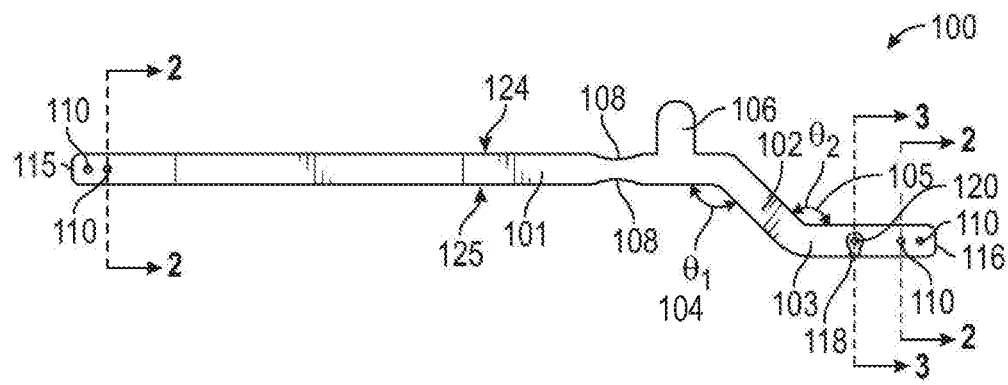
FIG. 1 is a top plan view illustrating a pectus bar in accordance with various embodiments.

The drawing figures described herein are for illustrative purposes only of selected embodiments and not of all possible implementations, and are not intended to limit the scope of any of the exemplary embodiments disclosed herein or any equivalents thereof.

DETAILED DESCRIPTION

The following detailed description of the invention is merely exemplary in nature and is not intended to limit the invention or the application and uses of the invention. Furthermore, there is no intention to be bound by any theory presented in the preceding background or the following detailed description.

Figure 2:
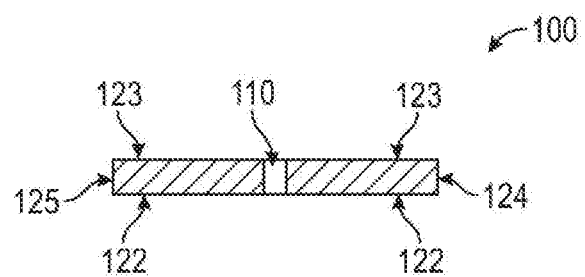
FIG. 2 is a cross-sectional view along the line 2-2 of FIG. 1 in accordance with various embodiments.
Figure 3:
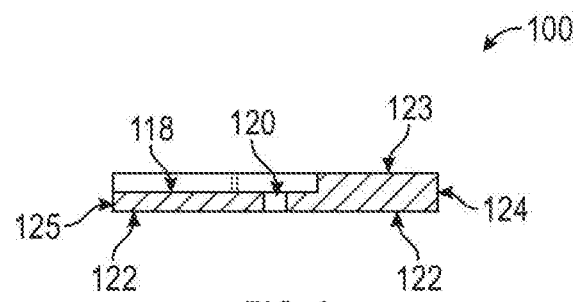
FIG. 3 is a cross-sectional view along the line 3-3 of FIG. 1 in accordance with various embodiments.

FIG. 1 is a top plan view illustrating a pectus bar 100 in accordance with various embodiments, FIG. 2 is a cross-sectional view through section 2-2 of FIG. 1, and FIG. 3 is a cross-sectional view through section 3-3 of FIG. 1. Referring now to FIGS. 1-3, the exemplary pectus bar 100 is an elongated bar having an offset bend between a first end 115 and a second end 116. Although pectus bar 100 is illustrated as single contiguous component, the pectus bar 100 can be viewed as having three sections: an elongated section 101, an offset section 102, and a connection section 103. In the illustrated embodiment, the major axes of elongated section 101 and connection section 103 are substantially parallel to each other. The elongated section 101 extends from the first end 115 to the offset section 102, and the connection section 103 extends from the second end 116 to the offset section 102.

An angle 104 designates the transition from the offset section 102 to the elongated section 101, and is generally an obtuse angle ranging, for example, from 100 degrees to 150 degrees. In some embodiments, the angle 104 is in the range of 120 degrees to 130 degrees. An angle 105 designates the transition from the offset section 102 to the connection section 103. Since elongated section 101 and connection section 103 are substantially parallel, angle 104 is substantially equal to angle 105 in this embodiment.

In the illustrated embodiment, pectus bar 100 is generally a longitudinally extending bar of generally uniform thickness and a generally rectangular cross-section. The first end 115 and the second end 116 may include arcuate (rounded) ends, as shown, and generally includes a top surface 123, an opposing bottom surface 122, and a pair of opposing side surfaces 124, 125.

The pectus bar 100 may be provided in various sizes having a length between, for example, 7.0 inches to 15.0 inches with each size varying by about 0.5 inch. However, lengths of less than 7.0 inches and greater than 15.0 inches can be provided, if required for a specific patient.

In some embodiments, the thickness of pectus bar 100 (e.g., as viewed in FIGS. 2 and 3) may be in a range from 1.5 mm to 4.5 mm, and the width of pectus bar 100 is in a range from 5.0 mm to 25.0 mm. However, should there be enough clearance in a particular application, the pectus bar 100 may be thicker and/or wider, resulting in a bar that exhibits a higher bending stiffness and bending strength.

As illustrated in FIG. 1, the elongated section 101 includes a pair of apertures 110 near the first end 115. The apertures 110 are configured to receive sutures, metal wire, or the like to secure pectus bar 100 to a rib. With reference to FIG. 2, the apertures 110 can be cylindrical holes extending the entire thickness of the pectus bar 100.

Located on a distal end of the elongated section 101 is a stabilizer 106 extending (e.g., orthogonally) from the elongated section 101. The stabilizer 106 generally has the same thickness as the pectus bar 100 in region 101. In some embodiments, the width of stabilizer 106 is in the range of 0.5-1.0 inches, and its length is in the range of 1.0 to 2.0 inches. In some embodiments, the width of the stabilizer 106 is in the range from 0.6 inches to 0.85 inches and the length of the stabilizer 106 is in the range from 1.25 inches to 1.75 inches.

Between the first end 115 and the stabilizer 106 is a pair of opposing rib reveals 108. The length of the rib reveals 108 may be in a range of 0.75 inches to 2.5 inches. The rib reveals 108 are illustrated as an arc; however, the rib reveals 108 may be curved on the ends and flat in between. The rib reveals 108 are configured to provide space between the pectus bar 100 and a bottom portion of a rib. The rib reveal 108 are thereby configured to provide relief to the intercostal nerve, which runs in a channel below the rib. Designs of previous, prior art pectus bars typically have straight edges running below the ribs, which can, over time, pinch the intercostal nerve against the rib, which can cause significant pain to the patient.

The connection section 103 includes a pair of apertures 110 near the second end 116. As previously described, the apertures 110 are configured to receive sutures or metal wire to secure pectus bar 100 to a rib.

Between the second end 116 and the angle transition 105 is a connector channel 118. FIG. 3 illustrates the connector channel 118 in a cross-sectional view along the line 3-3 of FIG. 1, and illustrates an embodiment in which connector channel 118 is recessed below the top surface 123. The connector channel 118 is configured to receive a connector (described in further detail below) which when engaged (via a hole or other opening 120), has a top surface that is flush with the top surface 123 of the pectus bar 100.

In accordance with various embodiments, the pectus bar 100 is provided in a straight or flattened condition, which is subsequently shaped (manually or via automation) to match a desired chest contour during surgery. However, in some embodiments, the pectus bar 100 is tilted by 15 degrees to 25 degrees at a point between the stabilizer 106 and the rib reveal 108 in the elongated section 101.

Figure 4:
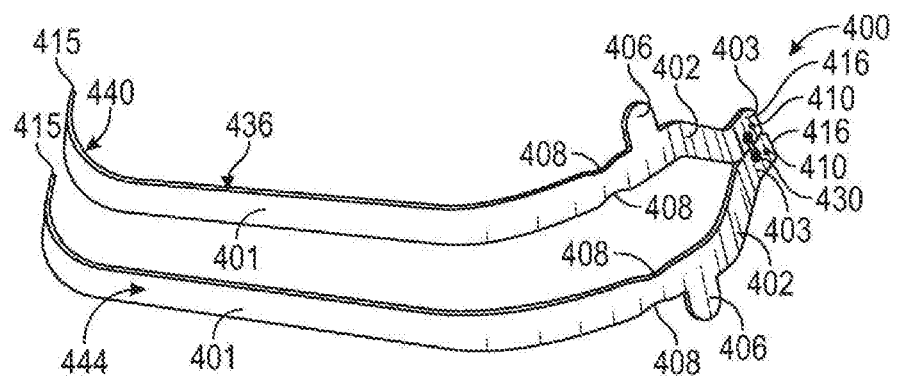
FIG. 4 is an elevated perspective view illustrating an apparatus for treating pectus excavatum in accordance to various embodiments.

FIG. 4 is an elevated perspective view illustrating a pectus bar apparatus 400 for treating pectus excavatum in accordance to various embodiments. The pectus bar apparatus 440 comprises a pair of pectus bars 440, 444, which are substantially mirror images of each other. In some embodiments, however, the pair of pectus bars 440, 444 are not substantially mirror images. For example, the top pectus bar 440 may be curved as illustrated by arrow 436, and the bottom pectus bar 444 may be straight or significantly straighter than pectus bar 440.

The pectus bars 440, 444 are similar to pectus bar 100 previously described. Each of the pectus bars 440, 444 is a contiguous elongated bar having an offset bend between a first end 415 and a second end 416. Each of the pectus bars 440, 444 have plurality of apertures 410 at either end. Each of the pectus bars 440, 444 can viewed as having three sections: an elongated section 401, an offset section 402, and a connection section 403.

Each of the pectus bars 440, 444 are shaped to match a desired chest contour for a particular patient, and each includes a pair of rib reveals 408 and a stabilizer 406. The pectus bars are secured together by connector system 430, having a top surface, which is flush with a top surface of each of the pectus bars 440, 444.

Figure 5:
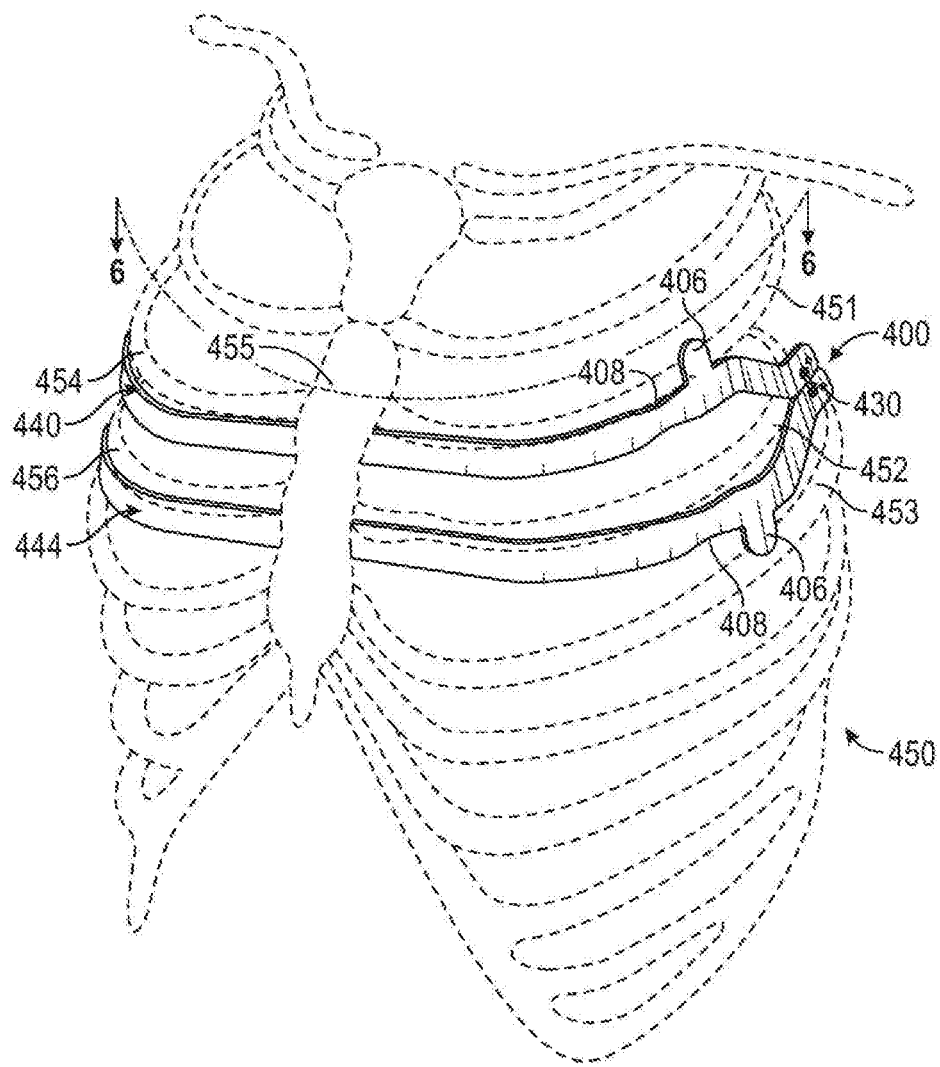
FIG. 5 is an elevated perspective view illustrating the apparatus for treating pectus excavatum in relation to a rib cage in accordance to various embodiments.

Referring to FIG. 5, an elevated perspective view of the pectus bar apparatus 400 illustrated in relation to a rib cage 450. Each of the top pectus bars 440 and the bottom pectus bar 444 is inserted into the patient individually. In this illustration, the top pectus bars 440 and the bottom pectus bar 444 are substantially mirror images of each other.

With attention to the top pectus bar 440, the stabilizer 406 is in contact with an outer portion of rib 451. The top pectus bar 440 crosses into the rib cage 450 at the rib reveal 408, which is in minimal contact with rib 451. The bar 440 is placed under the sternum 455 to support the chest cavity in the post treatment position, which has mitigated or removed the depression. The bar 440 crosses underneath rib 454 and back to the outside of the rib cage 450. The first end 415 of the pectus bar 440 is secured to rib 454 with sutures or metal wire through at least one of the apertures 410 and around the rib 454.

Moving to the bottom pectus bar 444, the stabilizer 406 is in contact with an outer portion of rib 453. The bottom pectus bar 444 crosses into the rib cage 450 at the rib reveal 408, which is not in contact with rib 453. The bottom bar 444 is placed under the sternum 455 to support the chest cavity in the post treatment position. The bar 440 crosses underneath rib 454 and back to the outside of the rib cage 450. The first end 415 of the bottom pectus bar 444 is secured to rib 456 with sutures or metal wire through at least one of the apertures 410 and around the rib 456.

The connection system 430 securely connects the top pectus bar 440 and the bottom pectus bar 444. The connection system 430 substantially prevents movement (relative to each other as well as relative to rib cage 450) of either of the pectus bars 440, 444. After the connection system 430 is completely engaged with pectus bars 440, 444, the pectus bar apparatus 400 effectively becomes a single, rigid unit. The second ends 416 of the pectus bars 440, 444 are secured to rib 452 with sutures or metal wire through at least one of the apertures 410 and around the rib 452.

Figure 6:
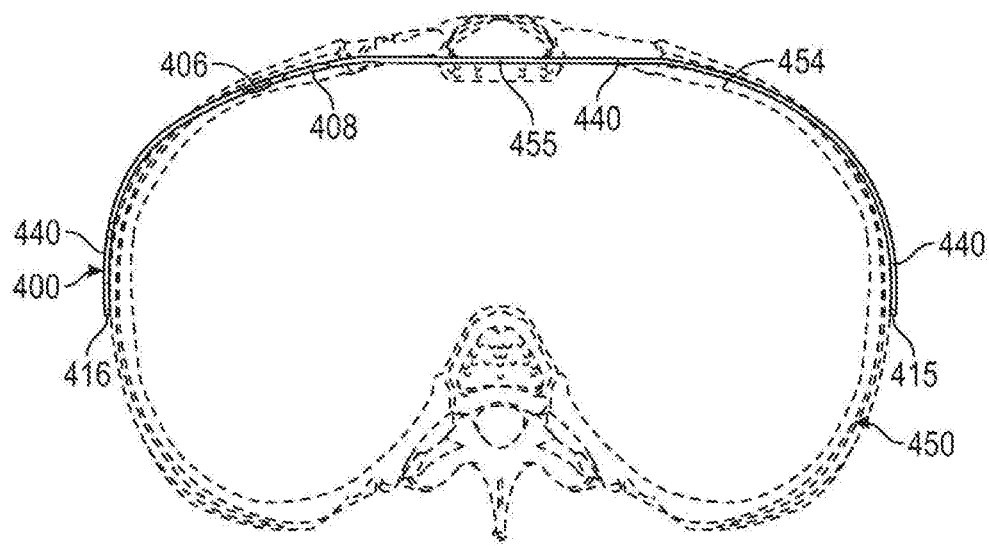
FIG. 6 is a cross-sectional view along the line 6-6 of FIG. 5 in accordance to various embodiments.
Figure 7:
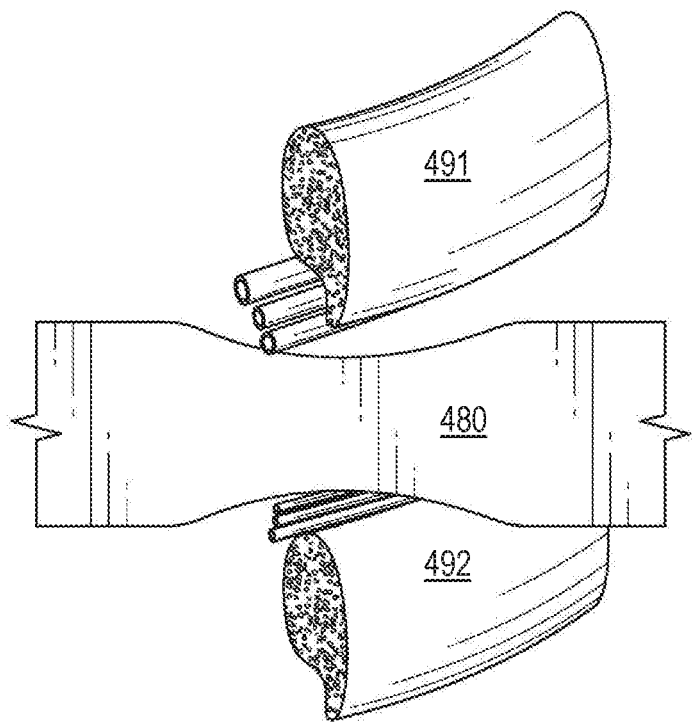
FIG. 7 is a partial cut-away view of a pectus bar positioned between a pair of ribs in accordance with one embodiment.

Referring to FIG. 6, the top pectus bar 440 is illustrated in a cross-sectional view along the line 6-6 of FIG. 5. As shown, the stabilizer 406 is in contact with an outer portion of rib 451. The top pectus bar 440 crosses into the rib cage 450 at the rib reveal 408, which is in minimal contact with rib 451. The bar 440 is placed under the sternum 455 to support the chest cavity in the post treatment position, which has mitigated or removed the depression. The bar 440 crosses underneath rib 454 and back to the outside of the rib cage 450. The first end 415 of the pectus bar 440 is secured to rib 454. In this regard, FIG. 7 is a partial cut-away view of a pectus bar 480 positioned between a pair of ribs 491 and 492 in accordance with one embodiment.

Figure 8:
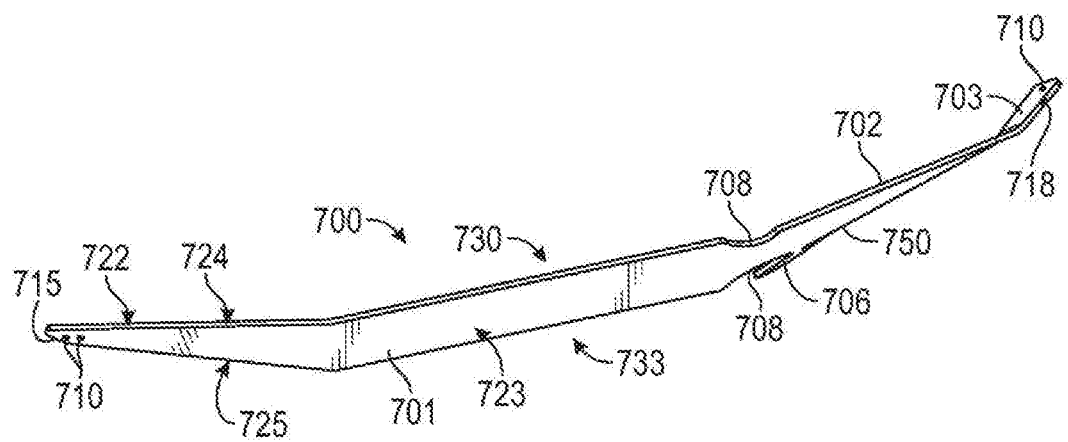
FIG. 8 is perspective view of a pectus bar illustrating a fold configured to be a convergence of two different planes of the pectus bar in accordance with various embodiments.
Figure 9:
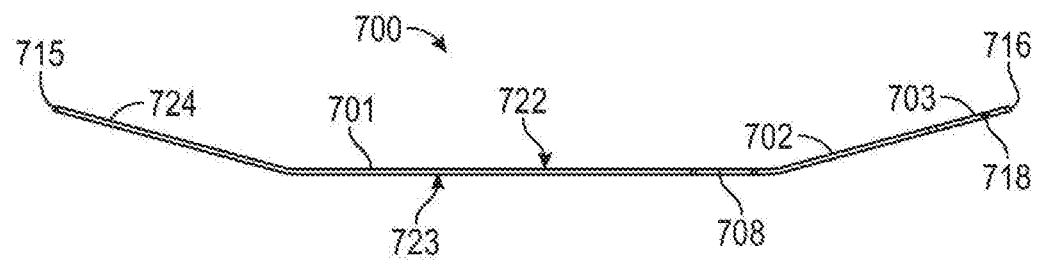
FIG. 9 is a bottom view of the pectus bar illustrated in FIG. 7 in accordance to various embodiments.

FIGS. 8 and 9 illustrate a pectus bar 700 in a pre-surgery configuration, including a tilt, which results in two different planes along the length of the bar 700. The pectus bar 700 is similar to pectus bar 100, as previously described. The pectus bar 700 is a contiguous elongated bar having an offset bend between a first end 715 and a second end 716 and having twist at a break 750. The pectus bar 700 has plurality of apertures 710 at either end. As discussed previously, the pectus bar 700 can be viewed in three sections; an elongation section 701, an offset section 702, and a connection section 703.

The pectus bar 700 includes a top surface 723 and an opposing bottom surface 722. The pectus bar 100 includes a pair of opposing side surfaces 724, 725. The connector channel 718 is recessed below the top surface 723.

The break 750 is configured to be a convergence of two different planes of the pectus bar 700. The pectus bar 700 is tilted by 15 degrees to 25 degrees at the break 750, which is between the stabilizer 706 and the rib reveal 708 in the elongated section 701. In some preferred embodiments, the tilt is 20 degrees. As illustrated in FIG. 8, the side surface 724 on a plane that is represented by the page of the figure. However, the pectus bar 700 left of the break 750, which includes the offset section 702 and the connection section 703, is on a plane that goes into the page at an angle, which can be recognized as the break 750 being on the page of the figure and the second end 716 is the point farthest into the page.

Although the pectus bar 700, in a pre-surgery configuration, includes a tilt, two of the pectus bars 700 can be shaped into mirror images of each other. For example, one pectus bar 700 can be shaped with force on the backside of the bar as indicated by arrow 730, which creates an arc shape extending out of the plane of the image of FIG. 8. The second pectus bar 700 can be shaped with force on the front side of the bar as indicated by arrow 733, which creates an arc shape going into the plane of the image of FIG. 8. However, if the other pectus bar 700 is flipped over so the arc shape is extending out of the paper, one will note the pectus bar 700 modified using force 733 and the pectus bar 700 modified using force 730 are substantially mirror images.

Figure 10:
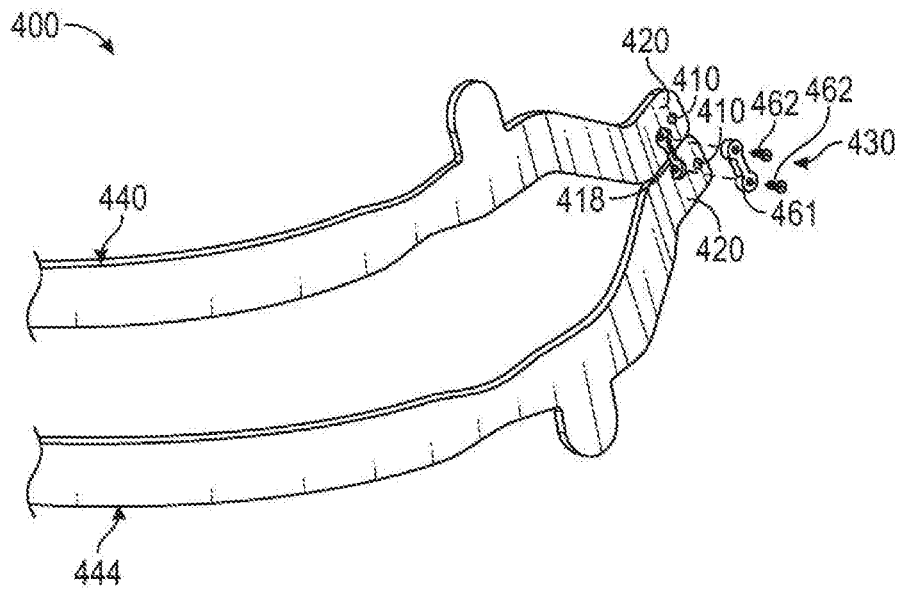
FIG. 10 is a perspective fragmented view illustrating fastening components of the apparatus for treating pectus excavatum in accordance to various embodiments.

FIG. 10 is a perspective partial view illustrating fastening components of an example fastening system 430. In this embodiment, a connector 461 of suitable shape and size is provided such that it received by connector channel 418 snuggly, like a puzzle piece. In one embodiment, the connecter 461 is fastened to the top pectus bar 440 and the bottom pectus bar 444 with screws 462 or other fasteners extending through holes 420 of each bar 440, 444. When the connector system 430 (which includes connector 461 and screws 462) is properly installed in connector channel 418, the top surfaces of the screws 462 and the connector 461 are flush with the top surface of each of the pectus bars 440, 444. In some of the kits envisioned herein, a plurality of connectors 461 of different lengths are included to accommodate a range of rib-cage geometries.

Figure 11:
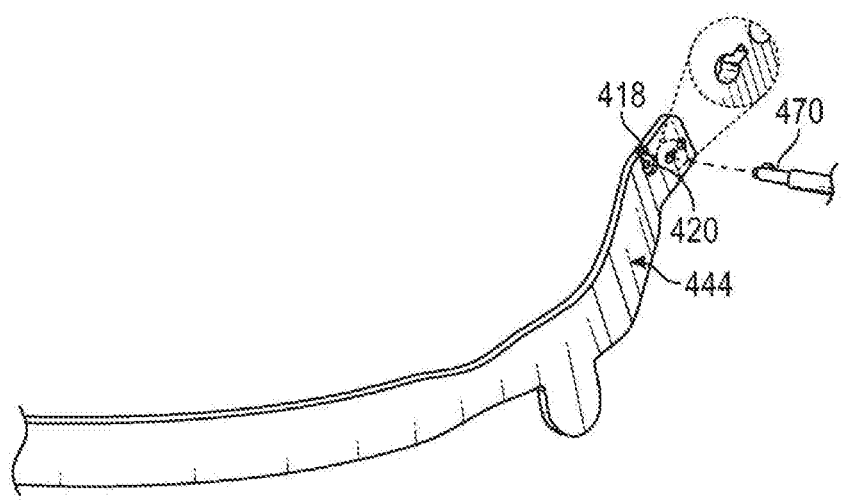
FIG. 11 is a perspective fragmented view illustrating a tool for positioning a pectus bar in a patient in accordance to various embodiments.

FIG. 11 is a perspective fragmented view illustrating a tool 470 for positioning a pectus bar 444 in a patient. In one embodiment, the size of tool 470 is about the same as a standard size screwdriver. Tool 470 is inserted within a corresponding tool opening in pectus bar 444 as shown, and is manipulated in such a way that pectus bar 444 is flipped up" to support a sternum. Tool 470 may be provided as part of an overall pectus bar kit. The tool opening may correspond to one of the apertures already incorporated into the pectus bar, or may be a special purpose opening provided specifically for that purpose.

Figure 12A:
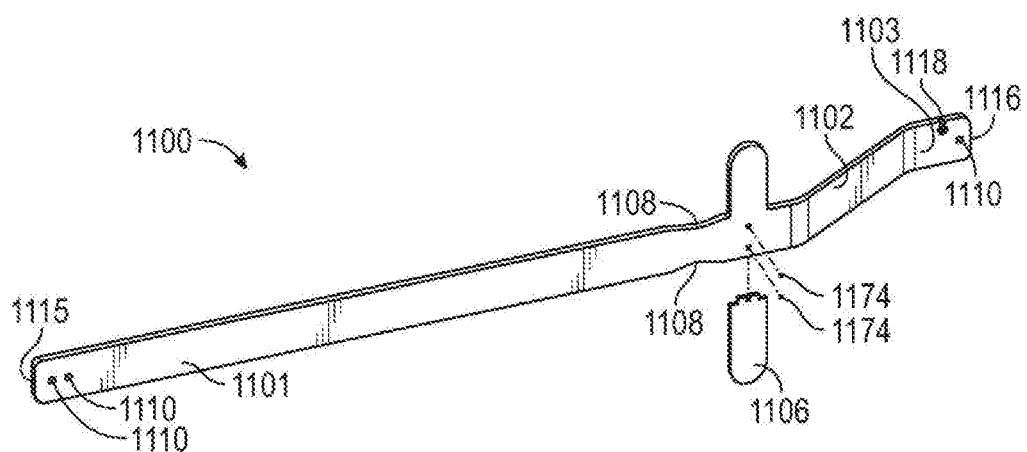
FIGS. 12A and 12B are perspective views illustrating an attachable stabilizer in accordance to various embodiment.
Figure 12B:
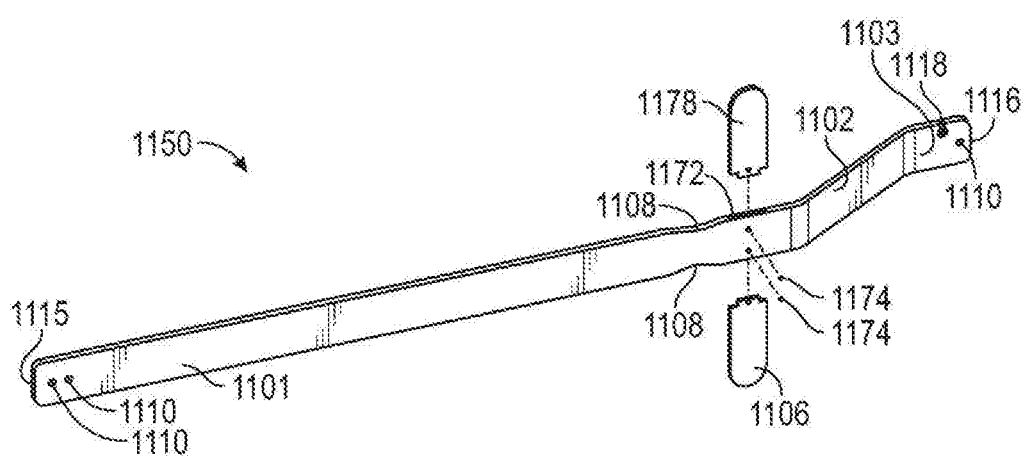

FIGS. 12A-12B are perspective views of pectus bars 1100 and 1150 illustrating attachable stabilizers in accordance with various embodiments. Pectus bar 1100 and 1150 are similar in many respects to pectus bar 100 and the other pectus bars as previously described. The pectus bar 1100 is a contiguous elongated bar having an offset bend between a first end 1115 and a second end 1116. The pectus bar 1100 has plurality of apertures 1110 at either end. As discussed herein, the pectus bar 1100 can be viewed in three sections: an elongation section 1101, an offset section 1102, and a connection section 1103. The connector channel 1118 is recessed below the top surface of the pectus bar 1100.

The pectus bar 1100 includes a recess (not illustrated), which is keyed to couple to attachable stabilizer 1106. The stabilizer 1106 may be secured to the pectus bar 1100 with one or more screws 1174. When the attachable stabilizer 1106 is properly installed, a top surface of the stabilizer is flush with a top surface of the pectus bar 100. FIG. 12B is an alternate embodiment that includes two attachable stabilizers 1178 and 1106 configured to be secured (via corresponding recesses, such as 1172) to opposing sides of stabilizer bar 1150.

Figure 13:
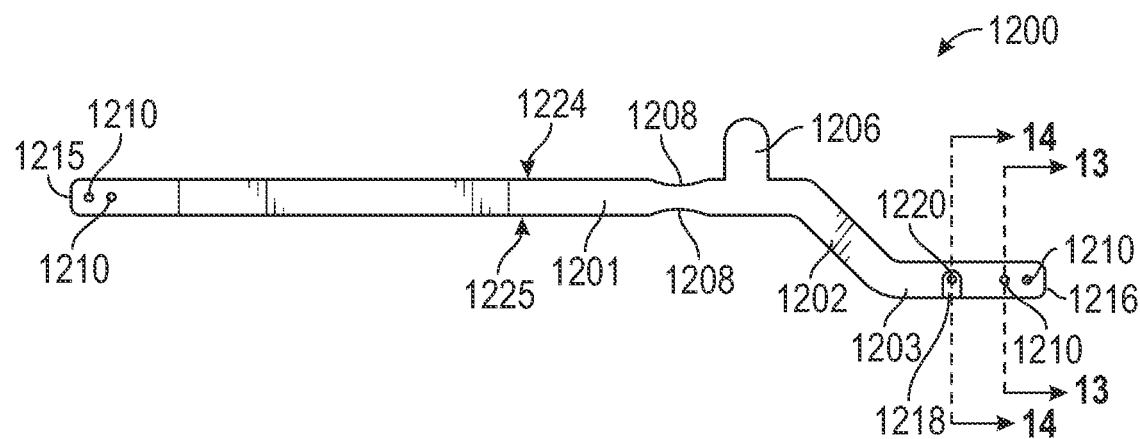
FIG. 13 is top plan view illustrating a pectus bar with an enlarged fastening channel in accordance with various embodiments.

FIG. 13 is top plan view illustrating a pectus bar with an enlarged fastening channel. Pectus bar 1200 is similar to pectus bar 100 and the other pectus bars, as previously described. The pectus bar 1200 is also a contiguous elongated bar having an offset bend between a first end 1215 and a second end 1216. The pectus bar 1200 has plurality of apertures 1210 at either end, a stabilizer 1206, a hole 1220 in connector channel 1218, opposing side surfaces 1224 and 1225. As discussed herein, the pectus bar 1200 can be viewed in three sections: an elongation section 1201, an offset section 1202, and a connection section 1203.

Figure 14:
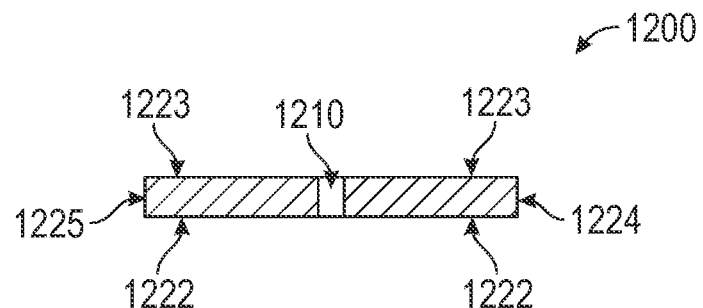
FIG. 14 is a cross-sectional view along the line 13-13 of FIG. 13 in accordance with various embodiments.

A first pair of apertures 1210 is located near the first end 1215 and a second pair of apertures 1210 is located near the second end 1216. The apertures 1210 are configured to receive sutures or metal wire to secure pectus bar 1200 to a rib. With reference to FIG. 14, the apertures 1210 can be cylindrical holes thru the thickness of the pectus bar 1200 (extending from top surface 1223 to bottom surface 1222).

Figure 15:
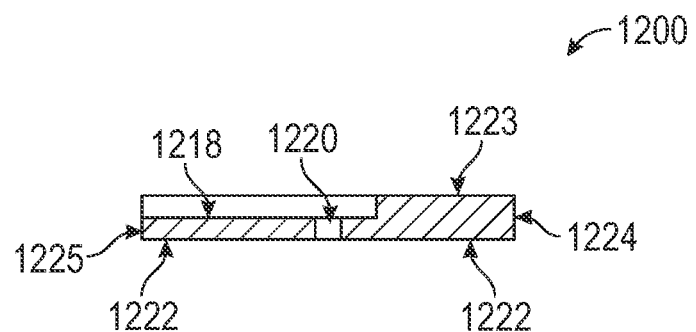
FIG. 15 is a cross-sectional view along the line 14-14 of FIG. 13 in accordance with various embodiments.

Referring to FIG. 15, the connector channel 1218 is recessed below the top surface of the pectus bar 1200. In this configuration, the connector channel 1218 is larger, which can allow for some adjustment if two pectus bars 1200 cannot be perfectly aligned within the patient's body.

FIG. 14 illustrates the connector channel 1218 in a cross-sectional view along the line 14-14 of FIG. 12. As shown, the connector channel 1218 is recessed below the top surface 1223. The connector channel 1218 is configured to receive a connector, which when engaged, has a top surface that is flush with the top surface 1223 of the pectus bar 1200.

Figure 16:
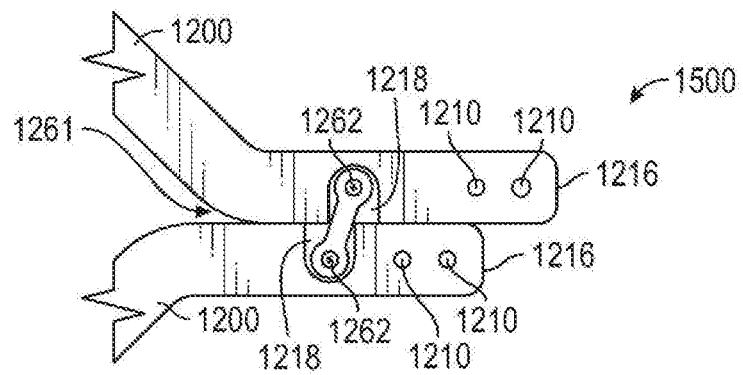
FIG. 16 is partial side view of an alternative connection system in accordance with various embodiments.

FIG. 16 is partial side view of connector channel 1218 and connector 1261 engaged within two pectus bars 1200, which are not perfectly aligned with each other—i.e., the channel openings 1218 are slightly offset laterally. In this example embodiment 1500, a number of different sized connectors 1261 may be included with a pectus bar kit, which allows the surgeon flexibility in connecting the two pectus bars 1200 (e.g., via screws 1262). Also illustrated are apertures 1210 adjacent to second end 1216.

Figure 17:
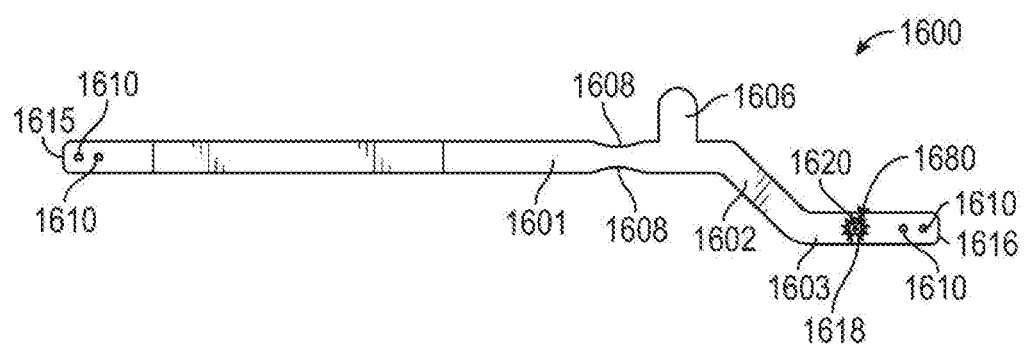
FIG. 17 is top plan view illustrating a pectus bar with an enlarged fastening channel and teeth in accordance with various embodiments.

FIG. 17 is top plan view illustrating a pectus bar 1600 with an enlarged fastening channel 1618 with associated hole 1620 and plurality of internal teeth 1680 or other such geometrical features. As in previous embodiments, pectus bar 1600 is a contiguous elongated bar having an offset bend between a first end 1615 and a second end 1616. The pectus bar 1600 has plurality of apertures 1610 at either end. As discussed herein, the pectus bar 1600 can be viewed in three sections: an elongation section 1601, an offset section 1602, and a connection section 1603. The pectus bar 1600 has a pair of rib reveals 1608 and a stabilizer 1606.

The connector channel 1618 is recessed below the top surface of the pectus bar 1600. In this configuration, the connector channel 1618 is larger and has a plurality of teeth 1680 distributed within the top of the are of channel 1618, which can allow for rotational adjustment if two pectus bars 1600 cannot be perfectly aligned in the body. The plurality of teeth 1680 can interlace with a plurality of connector teeth 1681 on connector 1662, which can lock the connector 1662 into place and ensure that there is no movement between pectus bars.

Figure 18A:
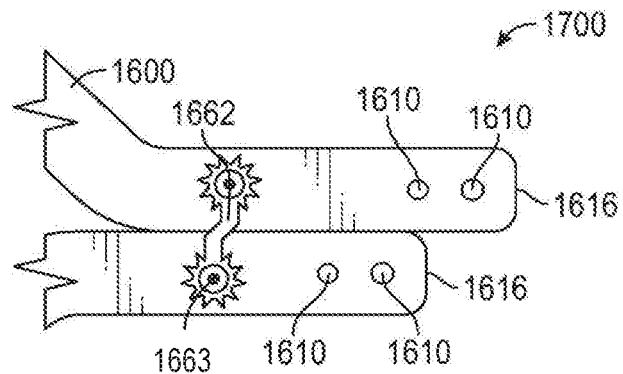
FIGS. 18A and 18B are partial side views of a second alternative connection system in accordance with various embodiments.
Figure 18B:
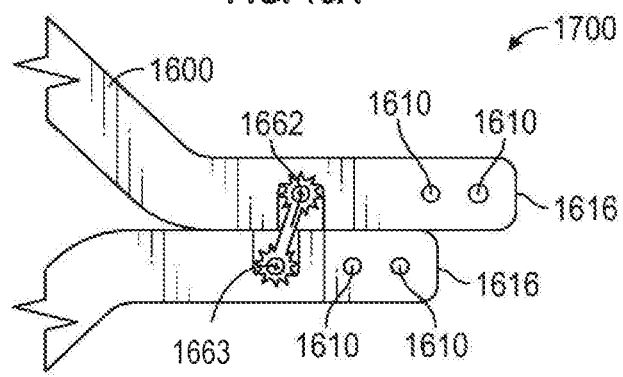

FIGS. 18A and 18B are partial side views of an embodiment 1700 in which the connector channel 1618 and connector 1661 are engaged on two pectus bars 1600, which are not perfectly aligned with each other. In this configuration, the connector channel 1618 is larger and has a plurality of teeth 1680 in the top of the are of channel 1618, which allows for some adjustment of the relative positions of pectus bars 1600. The plurality of teeth 1680 can interlace with a plurality of connector teeth 1681 on connector 1662, which can lock the connector 1662 into place and ensure that there is no movement between pectus bars. Screws or other fasteners 1663 may be used to secure connector 1662 relative to pectus bars 1600. FIG. 21F illustrates a variation 2080 of such an embodiment.

Figure 19:
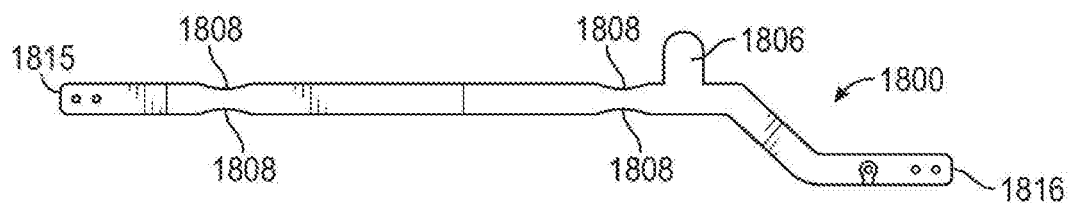
FIG. 19 is a top plan view illustrating a pectus bar having an addition set of rib reveals in accordance to various embodiments.

FIG. 19 is a top plan view illustrating a pectus bar 1800 having an addition set of rib reveals 1808 in accordance to various embodiments. Pectus bar 1800 is also a contiguous elongated bar having an offset bend between a first end 1815 and a second end 1816. The pectus bar 1800 has plurality of apertures at either end, as in the previous embodiments. The pectus bar 1800 has a pair of rib reveals 1808 and a stabilizer 1806. The pectus bar 1800 includes a second pair of rib reveals 1808 located towards the first end 1815. The second pair of rib reveals 1808 are positioned in the bar 1800 for interfacing with a rib bone where the bar 1800 crosses back over from inside the rib cage to outside of the rib cage. As discussed herein, the rib reveal 1808 relieves the rib of painful pressure and prevents the intercostal nerve from being pinched against a rib by the bar.

Figure 20:
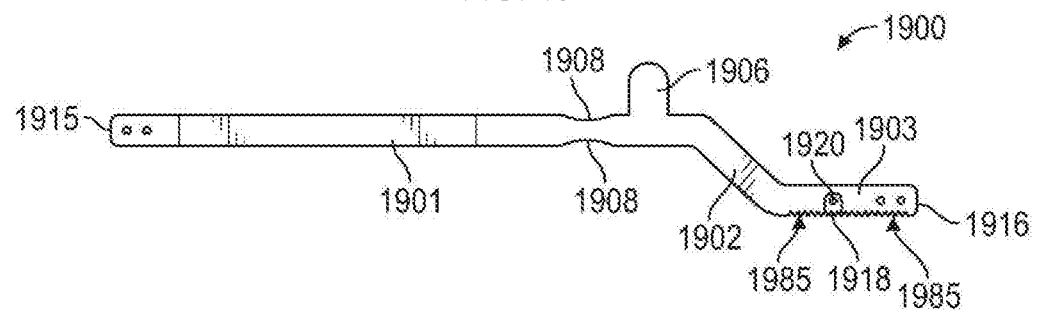
FIG. 20 is a top plan view illustrating a pectus bar having a saw toothed connection surface in accordance with various embodiments.

FIG. 20 is a top plan view illustrating a pectus bar 1900 having a saw toothed connection surface in accordance with various embodiments. The pectus bar 1900 is also a contiguous elongated bar having an offset bend between a first end 1915 and a second end 1916. The pectus bar 1900 has plurality of apertures at either end, as in the previous embodiments. As discussed herein, the pectus bar 1900 can be viewed in three sections: an elongation section 1901, an offset section 1902, and a connection section 1903. The pectus bar 1900 has a pair of rib reveals 1908 and a stabilizer 1906. In addition, a portion of a side surface of the connection section 1903 includes a hole 1920 and a plurality of saw teeth 1985 as shown.

FIGS. 21A-21G illustrate various example interconnect schemes that may be used in connection with one or more of the embodiments discussed above.

Figure 21A:
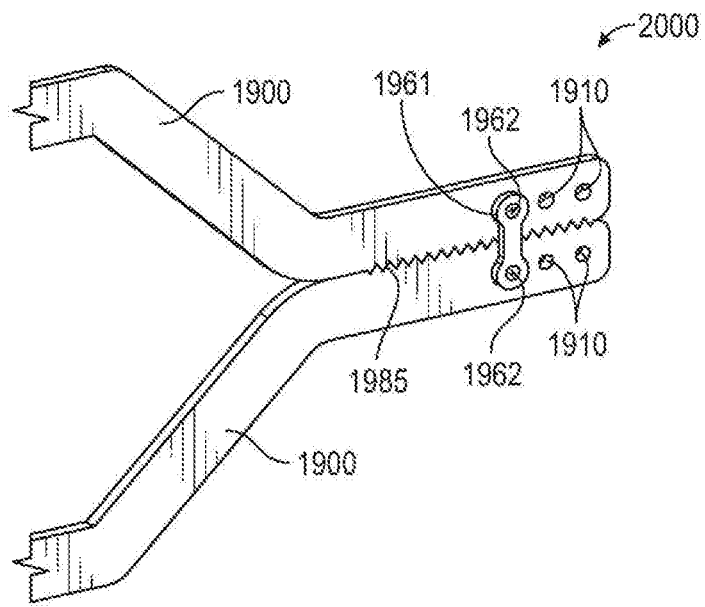
FIGS. 21A-21F depict example pectus bar interconnection schemes and components in accordance with various embodiments.
Figure 21B:
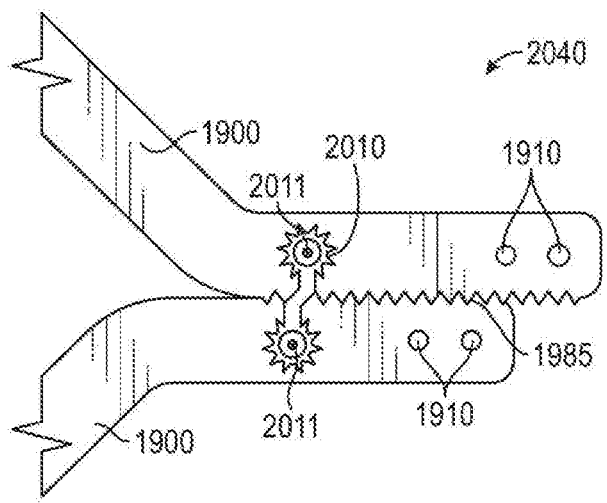

FIGS. 21A and 21B are partial side views of an alternative connection system (2000 and 2040) comprising a saw tooth configuration engaged on two pectus bars 1900, which are aligned (FIG. 21A) and not aligned (21B). The side surface of the connection section 1903 includes a plurality of saw teeth 1985, which can be positioned to be interlaces and lock the bars 1900 together and prevent relative lateral movement of the components. Connectors 1962, 2011 may utilized to secure connectors 1961 and 2010, as shown.

Figure 21C:
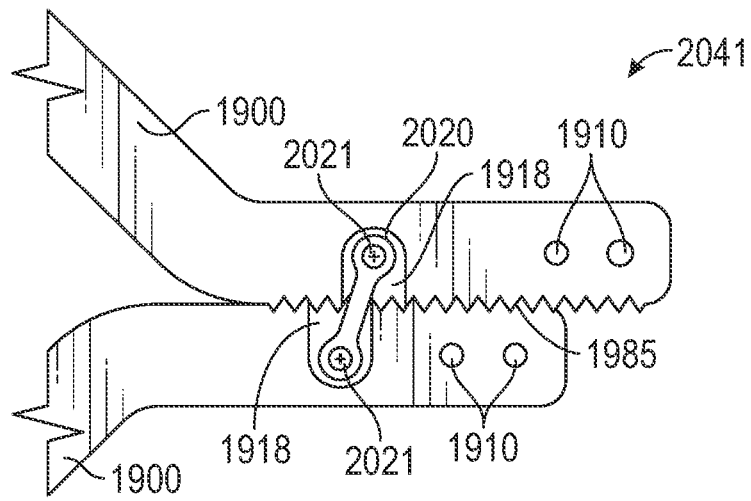

FIG. 21C illustrates an embodiment 2041 that also includes saw teeth 1985, in which a connector 2020 fits within a recessed opening 1918 as shown and is secured via screws 2021.

Figure 21D:
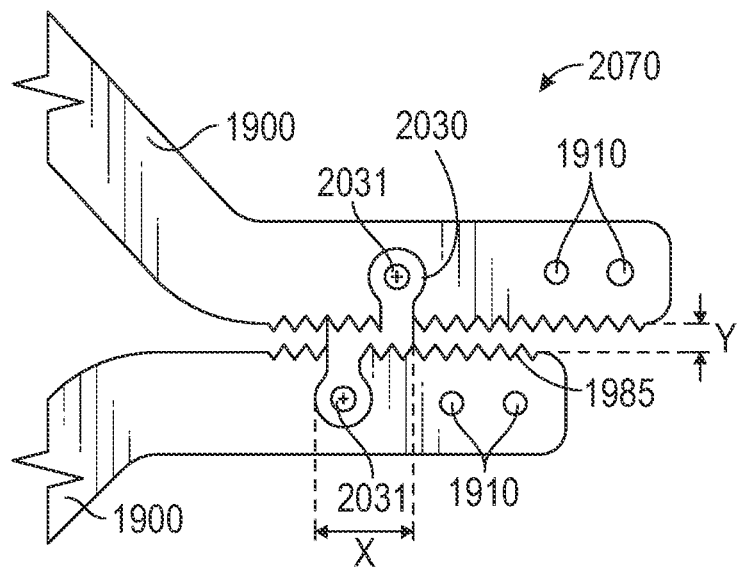
Figure 21E:
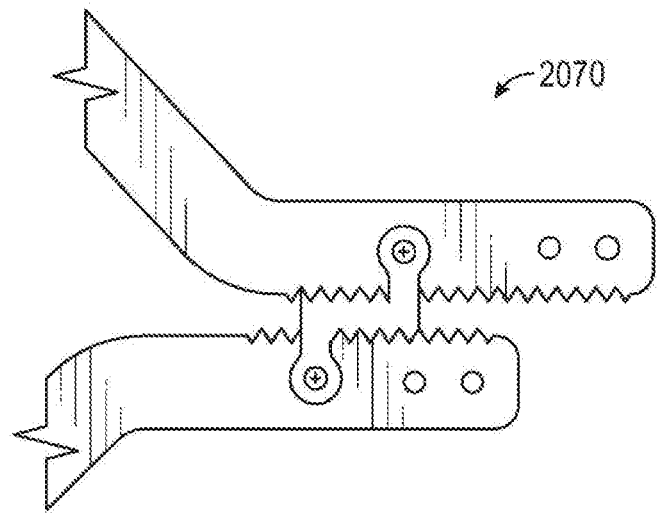
Figure 21F:
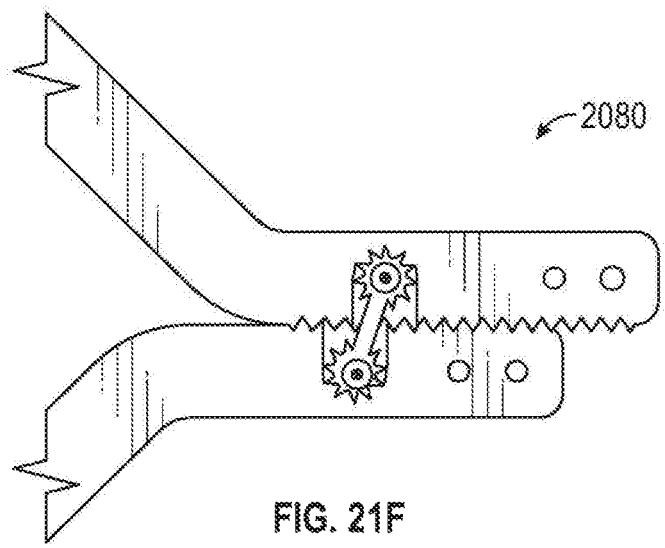
Figure 21G:
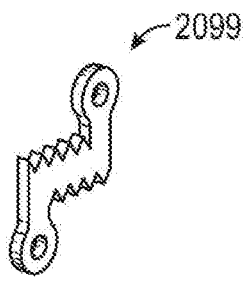

FIG. 21D illustrates an embodiment 2070 in which connector 2030 includes a middle linear section of length X that itself includes saw teeth on both sides that are configured to interface with saw teeth 1985 as shown when secured in place via screws 2031. This results in an offset distance Y perpendicular to the axis of saw teeth 1985, which may be selected to accommodate a particular rib cage geometry in which such an offset is desirable. Another example of this embodiment, in close-up, is shown in FIG. 21E, and FIG. 21G illustrates an example connector 2099 that may be used in conjunction with this interconnect scheme.

Figure 22:
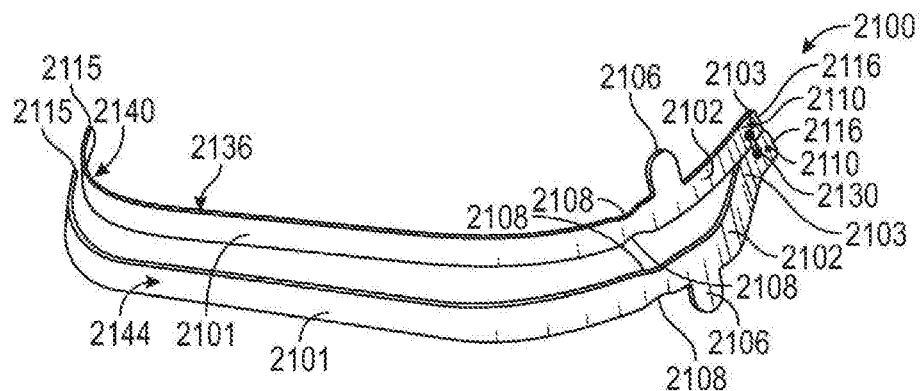
FIG. 22 is perspective view of a pectus bar in accordance with various embodiments.
Figure 23:
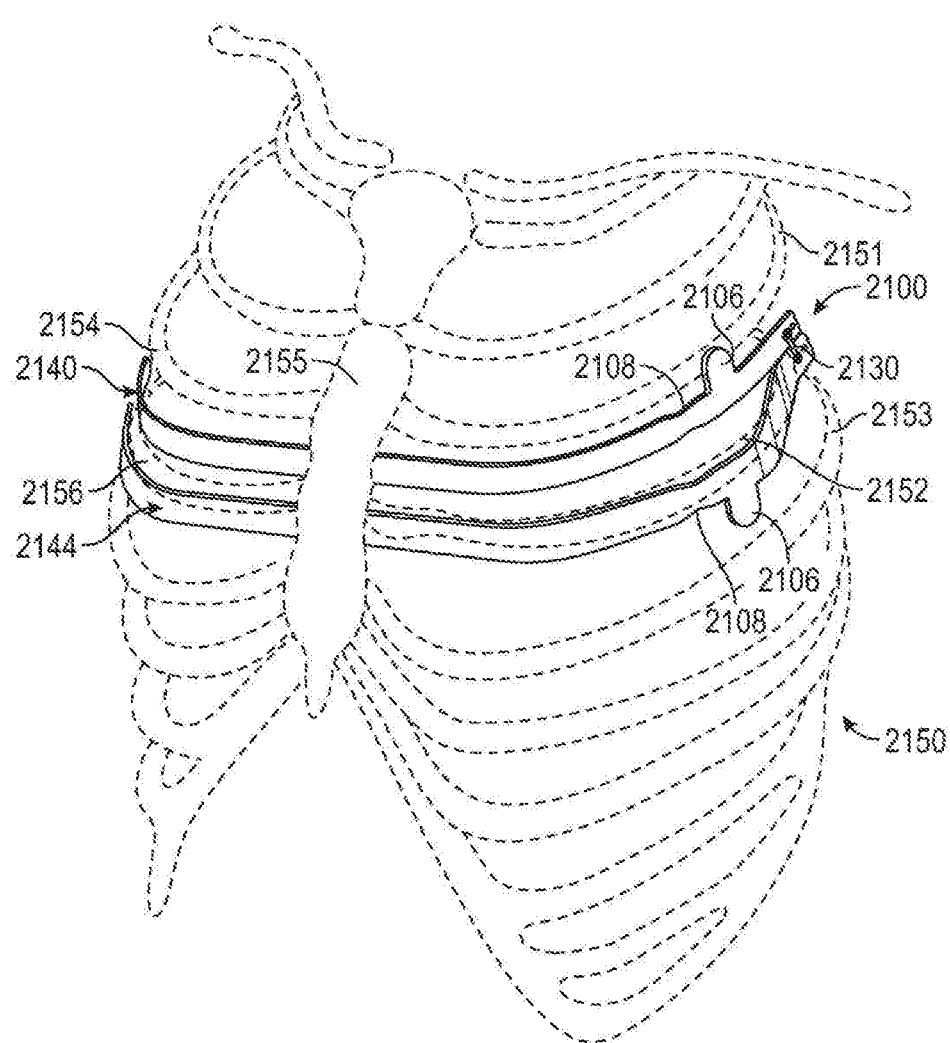
FIG. 23 illustrates the pectus bar apparatus of FIG. 22 as deployed within a rib cage in accordance with various embodiments.
Figure 24:
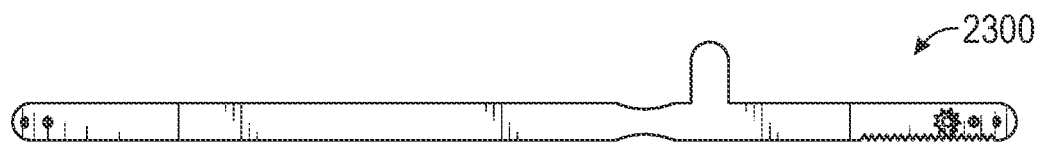
FIG. 24 is a partial side view of a pectus bar in accordance with various embodiments.
Figure 25A:
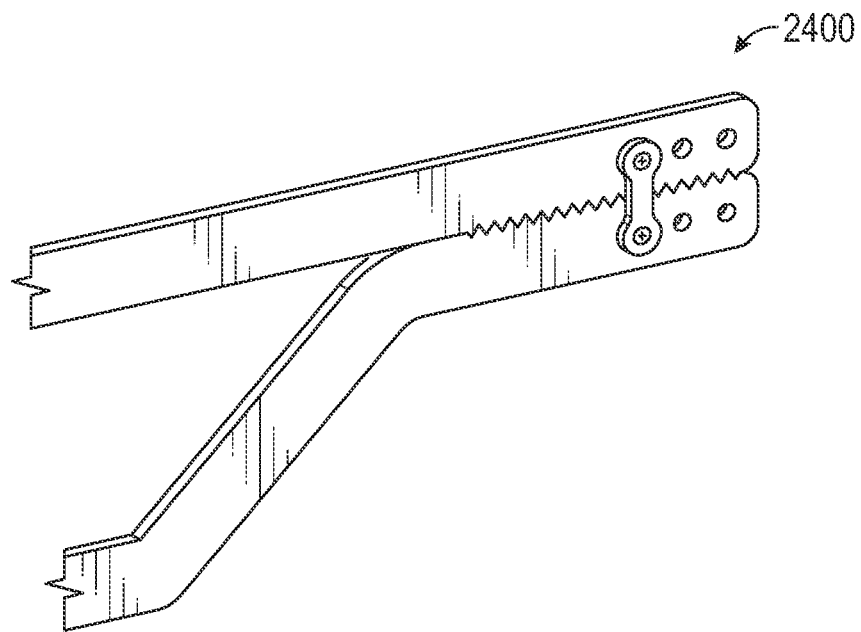
FIGS. 25A-25F depict pectus bar interconnection in accordance with various embodiments.
Figure 25B:
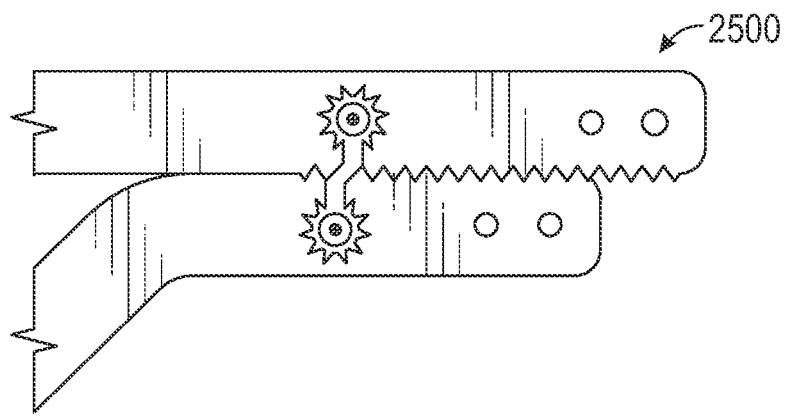
Figure 25C:
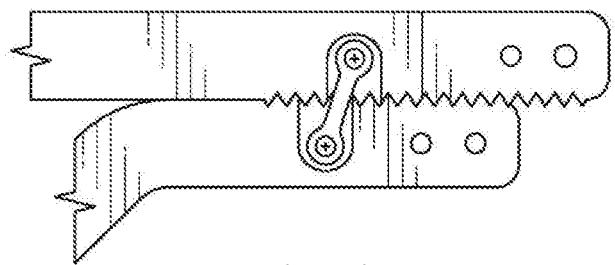
Figure 25D:
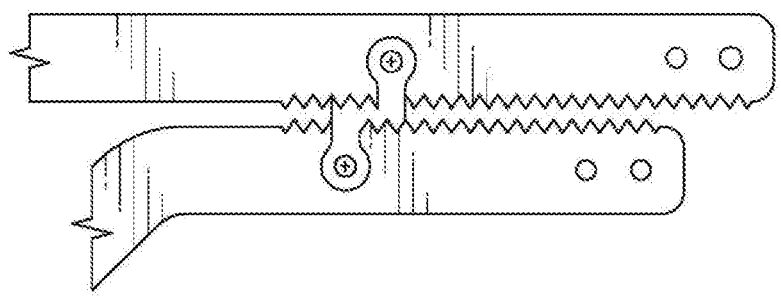
Figure 25E:
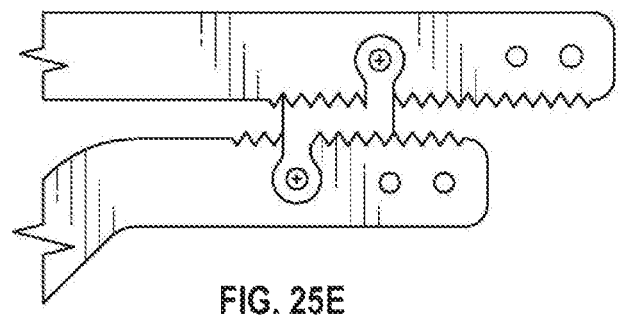
Figure 25F:
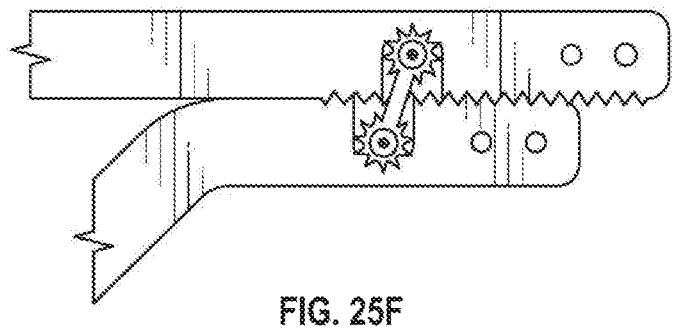

FIG. 22 illustrates a pectus bar assembly 2100 in accordance with an alternate embodiment, and FIG. 23 illustrates the pectus bar assembly 2100 provided within a ribcage 2150 (including, for example, ribs 2151, 2152, 2153, 2154, and 2156) and underneath sternum 2155. Consistent with the previously described embodiments, assembly 2100 includes an upper pectus bar 2136 and a bottom pectus bar 2144 coupled via a connector 2130, wherein each pectus bar includes an elongated section 2101, an offset section 2102, and a connection section 2103. Each pectus bar 2136 and 2144 has a first end 1115, a second end 2116, a plurality of apertures 2110, stabilizers 2106, and rib reveals 2108. In this embodiment (in comparison to the embodiment shown in FIGS. 4 and 5), the upper pectus bar does not include the angled offset bend previous described, while the bottom pectus bar 2144 does include the angled offset bend. Close-up images of such a system are shown in FIGS. 24, 25A, and 25B. That is, FIG. 24 illustrates a substantially straight upper bar 2300, FIG. 25A illustrates a substantially straight upper bar 2400 attached to a bottom bar via a connector as shown, wherein the mating portions of the pectus bars include a saw teeth portion, as described previously above. FIG. 25B illustrates a pectus bar 2500 featuring the use of a connector including teeth configured to mate with inner teeth provided in recessed portions as described previously above. Similarly, FIGS. 25C-25F illustrate the use of various connection schemes in connection with a straight upper bar, and are consistent with the embodiments described in the previous drawings.

Figure 26:
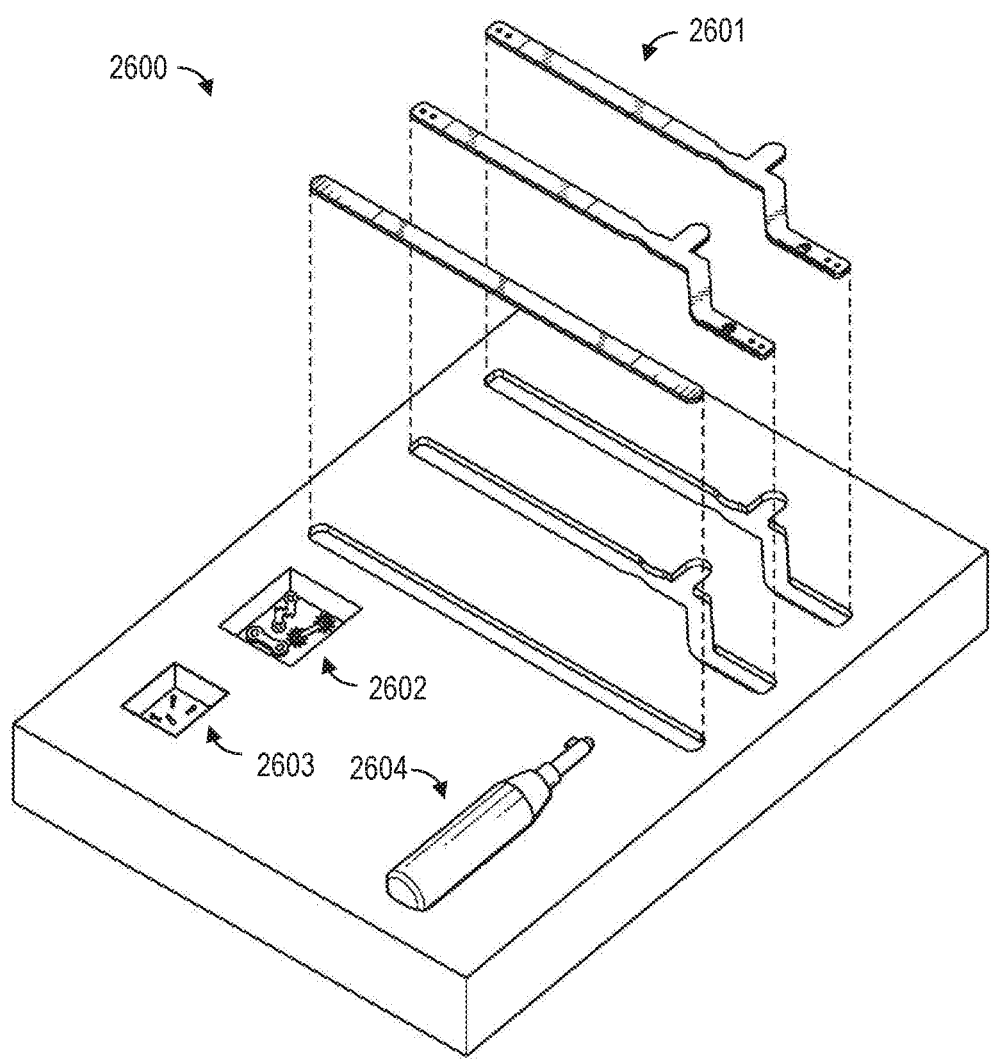
FIG. 26 illustrates a pectus bar kit in accordance with one embodiment.

FIG. 26 illustrates a pectus bar kit 2600 in accordance with various embodiments. More particularly, pectus bar kit 2600 includes a number of individual pectus bars 2601 (in this embodiment, two pectus bars with offsets and one substantially straight pectus bar), a number of connectors 2602 of various types (as described above), a number of screws or other fasteners 2603 for securing connectors 2602 to pectus bars 2601, and a tool 2604 that can be used to "flip" each pectus bar 2601 in place by removeably coupling to the pectus bar (e.g., by mechanically coupling to an end of the bar) such that the practitioner can then mechanically manipulate the tool to move the pectus bar into its deployed position.

Figure 27:
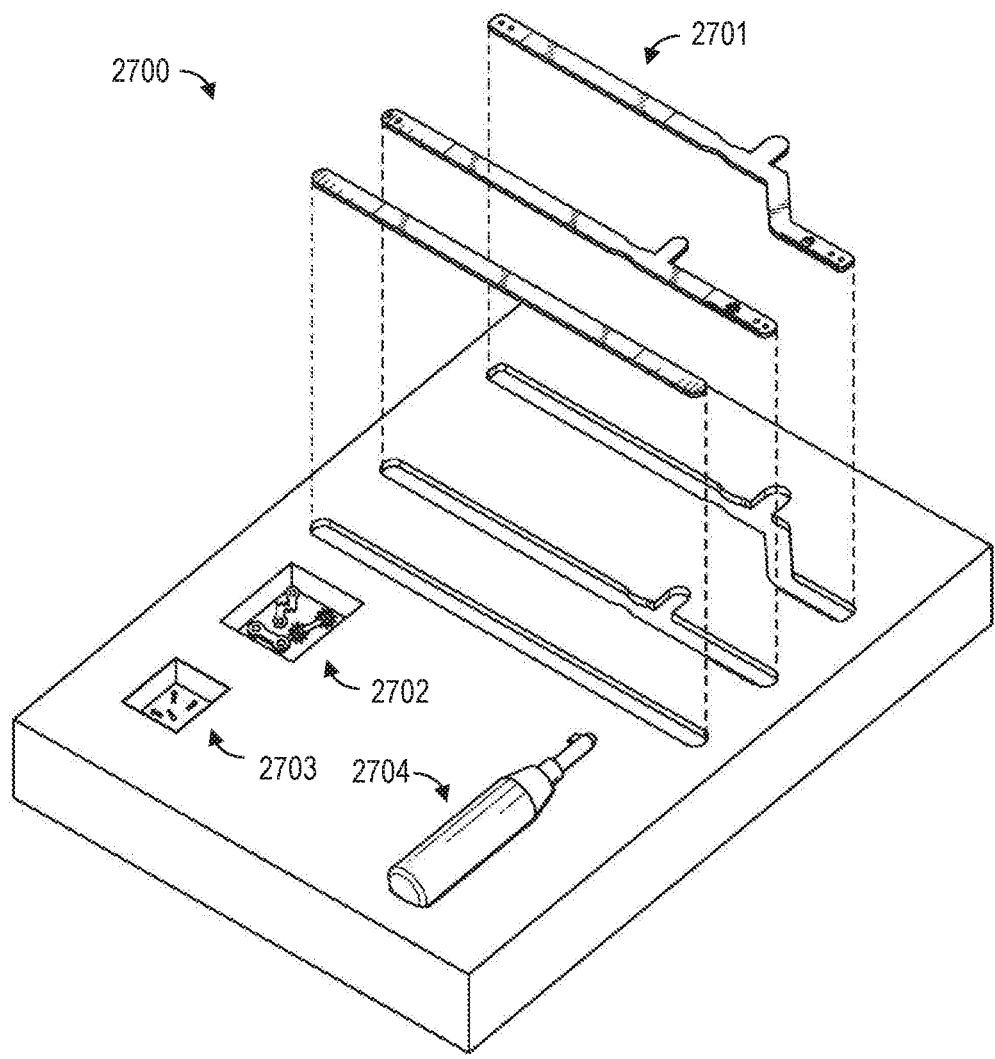
FIG. 27 illustrates a pectus bar kit in accordance with an alternate embodiment.

FIG. 27 illustrates an alternate embodiment of a kit 2700 including a number of pectus bars 2701, a number of connectors 2702, a number of fasteners 2703, and a tool 2704 as described above. In this embodiment, pectus bars 2701 includes two substantially straight bars, and one offset bar, as described above.

In summary, what has been described herein are various systems, methods, and kits for treating pectus excavatum that overcome the limitations of the prior art.

In one embodiment, a pectus bar apparatus includes: at least one elongated bar having an offset bend between a first end and a second end; at least one aperture near the first end and at least one aperture near the second end; a planar stabilizer extending orthogonally from the elongated bar; and a pair of opposing rib reveals located between the first end and the planar stabilizer.

In one embodiment, the apparatus includes a connector channel proximate the second end of the at least one elongated bar. A portion of a side of the at least one elongated bar may include a series of teeth. A second pair of rib reveals may also be provided between the first end and the planar stabilizer.

A pectus bar assembly in accordance with one embodiment includes: a first elongated bar having an offset bend between a first end and a second end, at least one aperture near the first end, at least one aperture near the second end, a planar stabilizer extending orthogonally from the elongated bar, a first connector channel, and a pair of opposing rib reveals located between the first end and the planar stabilizer of the first elongated bar; a second elongated bar having an offset bend between a first end and a second end, at least one aperture near the first end, at least one aperture near the second end, a planar stabilizer extending orthogonally from the elongated bar, a second connector channel, and a pair of opposing rib reveals located between the first end and the planar stabilizer of the second elongated bar; and a connector configured to be accepted by the first and second connector channels to thereby provide mechanical coupling of the first elongated bar to the second elongated bar; wherein each of the first and second elongated bars includes a tool opening configured to accept a tool adapted to manipulate the first and second elongated into place within a rib cage.

A pectus excavatum treatment method in accordance with one embodiment includes: providing access to a rib cage of a patient; inserting, within the rib cage, a first elongated bar having an offset bend between a first end and a second end, at least one aperture near the first end, at least one aperture near the second end, a planar stabilizer extending orthogonally from the elongated bar, a first connector channel, and a pair of opposing rib reveals located between the first end and the planar stabilizer of the first elongated bar; inserting, within the rib cage, a second elongated bar having an offset bend between a first end and a second end, at least one aperture near the first end, at least one aperture near the second end, a planar stabilizer extending orthogonally from the elongated bar, a second connector channel, and a pair of opposing rib reveals located between the first end and the planar stabilizer of the second elongated bar; manipulating, with a pectus bar tool, the first and second elongated bars such that they are correctly positioned and adjacent to each other within the rib cage; and securing a connector within the first and second connector channels to thereby provide mechanical coupling of the first elongated bar to the second elongated bar.

A pectus excavatum treatment kit in accordance with one embodiment includes: a first elongated bar having at least one aperture near the first end, at least one aperture near the second end, a planar stabilizer extending orthogonally from the elongated bar, a first connector channel, and a pair of opposing rib reveals located between the first end and the planar stabilizer of the first elongated bar; a second elongated bar having at least one aperture near the first end, at least one aperture near the second end, a planar stabilizer extending orthogonally from the elongated bar, a second connector channel, and a pair of opposing rib reveals located between the first end and the planar stabilizer of the second elongated bar; and a plurality of connectors, each configured to be accepted by the first and second connector channels to thereby provide mechanical coupling of the first elongated bar to the second elongated bar; a plurality of fasteners configured to mechanically secure one or more of the plurality of connectors to the connector channels of the first and second elongated bars; and a pectus bar tool; wherein each of the first and second elongated bars includes a tool opening configured to accept the tool adapted to manipulate the first and second elongated into place within a rib cage. In one embodiment, the first elongated bar includes an offset bend, and the second elongated bar is substantially straight. In another embodiment, the kit includes a third (either straight or offset) elongated bar.

As used herein, the word "exemplary" means "serving as an example, instance, or illustration." Any implementation described herein as "exemplary" is not necessarily to be construed as preferred or advantageous over other implementations, nor is it intended to be construed as a model that must be literally duplicated.

As used herein, the phrase "at least one of A, B, and C" can be construed to mean a logical (A or B or C), using a non-exclusive logical "or," however, can be contrasted to mean (A, B, and C), in addition, can be construed to mean (A and B) or (A and C) or (B and C). As used herein, the phrase "A, B and/or C" should be construed to mean (A, B, and C) or alternatively (A or B or C), using a non-exclusive logical "or."

It should be understood that steps within a method may be executed in different order without altering the principles of the present disclosure. For example, various embodiments may be described herein in terms of various functional components and processing steps. It should be appreciated that such components and steps may be realized by any number of hardware components configured to perform the specified functions.

While the foregoing detailed description will provide those skilled in the art with a convenient road map for implementing various embodiments of the invention, it should be appreciated that the particular embodiments described above are only examples, and are not intended to limit the scope, applicability, or configuration of the invention in any way. To the contrary, various changes may be made in the function and arrangement of elements described without departing from the scope of the invention.

The invention claimed is:

1. A pectus bar assembly comprising:
a first elongated bar having an offset bend between a first end and a second end, at least one aperture near the first end, at least one aperture near the second end, a planar stabilizer extending orthogonally from the elongated bar, a first connector channel, and a pair of opposing rib reveals located between the first end and the planar stabilizer of the first elongated bar;
a second elongated bar having an offset bend between a first end and a second end, at least one aperture near the first end, at least one aperture near the second end, a planar stabilizer extending orthogonally from the elongated bar, a second connector channel, and a pair of opposing rib reveals located between the first end and the planar stabilizer of the second elongated bar; and
a connector configured to be accepted by the first and second connector channels to thereby provide mechanical coupling of the first elongated bar to the second elongated bar;
wherein each of the first and second elongated bars includes a tool opening configured to accept a tool adapted to manipulate the first and second elongated into place within a rib cage.

2. The pectus bar assembly of claim 1, wherein at least one of the first and second elongated bars includes a connector channel proximate the second end of the at least one elongated bar, the connector channel configured to accept the connector such that the connector is substantially flush with a surface of the at least one elongated bar.

3. The pectus bar assembly of claim 1, wherein a portion of both the first and second connector channels includes a series of teeth, and the connector includes a corresponding series of connector teeth configured to mechanically interface therewith.

4. The pectus bar assembly of claim 1, wherein the first elongated bar includes a first saw tooth edge portion, the second elongated bar includes a second saw tooth edge portion, and the first and second saw tooth portions are configured to mechanically interlock when the pectus bar assembly is in a deployed state.

5. The pectus bar assembly of claim 1, wherein at least one of the first and second elongated bars includes a second pair of rib reveals between its first end and its planar stabilizer.

6. The pectus bar assembly of claim 1, wherein at least one of the planar stabilizers is removeably attachable to its respective elongated bar.

7. A pectus excavatum treatment kit comprising:
a first elongated bar having at least one aperture near the first end, at least one aperture near the second end, a planar stabilizer extending orthogonally from the elongated bar, a first connector channel, and a pair of opposing rib reveals located between the first end and the planar stabilizer of the first elongated bar;
a second elongated bar having at least one aperture near the first end, at least one aperture near the second end, a planar stabilizer extending orthogonally from the elongated bar, a second connector channel, and a pair of opposing rib reveals located between the first end and the planar stabilizer of the second elongated bar;
a plurality of connectors, each configured to be accepted by the first and second connector channels to thereby provide mechanical coupling of the first elongated bar to the second elongated bar;
a plurality of fasteners configured to mechanically secure one or more of the plurality of connectors to the connector channels of the first and second elongated bars; and a pectus bar tool;
wherein each of the first and second elongated bars includes a tool opening configured to accept the tool adapted to manipulate the first and second elongated into place within a rib cage.

8. The kit of claim 7, wherein the first elongated bar includes a first saw tooth edge portion, the second elongated bar includes a second saw tooth edge portion, and the first and second saw tooth portions are manipulated such that they are mechanically interlocked when the pectus bar assembly is deployed.

9. The kit of claim 7, wherein at least one of the planar stabilizers is removeably attached to its respective elongated bar.

10. The kit of claim 7, wherein at least a portion of the connectors includes peripheral teeth configured to interface with the connector channels of the first and second elongated bars.

11. The kit of claim 7, wherein the first elongated bar includes an offset bend, and the second elongated bar is substantially straight.

12. The kit of claim 7, further including a third elongated bar.

* * * * *